(12) United States Patent
Suh et al.

(10) Patent No.: US 6,444,796 B1
(45) Date of Patent: Sep. 3, 2002

(54) METHOD OF PREPARING FORM II CRYSTALS OF CLARITHROMYCIN

(75) Inventors: Kwee-Hyun Suh, Icheon-si; Mi-Ra Seong, Yongin-si; Nam-Du Kim, Osan-si; Gwan-Sun Lee, Seoul, all of (KR)

(73) Assignee: Hanmi Pharm Co., Ltd., Kyungki-do (KR)

( * ) Notice: Subject to any disclaimer, the term of this patent is extended or adjusted under 35 U.S.C. 154(b) by 0 days.

(21) Appl. No.: 09/693,795

(22) Filed: Oct. 20, 2000

(30) Foreign Application Priority Data

Oct. 21, 1999 (KR) .............................................. 99-45703

(51) Int. Cl.$^7$ ................................................. C07H 1/00
(52) U.S. Cl. ....................................... 536/7.2; 536/18.5
(58) Field of Search .................................. 536/7.2, 18.5

(56) References Cited

U.S. PATENT DOCUMENTS 5,274,085 A * 12/1993 Amano et al. ................ 536/7.4
5,844,105 A * 12/1998 Liu et al. ..................... 536/18.5

* cited by examiner

*Primary Examiner*—Elli Peselev
(74) *Attorney, Agent, or Firm*—Katten Muchin Zavis Rosenman

(57) ABSTRACT

Pure Form II crystals of clarithromycin can be prepared by a simple, high-yield process comprising the steps of treating crude clarithromycin or different crystal forms of clarithromycin with formic acid in an organic solvent to obtain crystalline clarithromycin formate and neutralizing the clarithromycin formate with a base in a mixture of water and a water-miscible organic solvent.

9 Claims, 3 Drawing Sheets

METHOD OF PREPARING FORM II CRYSTALS OF CLARITHROMYCIN

FIELD OF THE INVENTION

The present invention relates to a method of preparing pure Form II crystals of clarithromycin in a high yield; and crystalline clarithromycin formate used therein.

BACKGROUND OF THE INVENTION

Clarithromycin, 6-O-methylerythromycin A, is a semi-synthetic macrolide antibiotic of formula (I) which exhibits strong antibacterial activity toward a wide range of bacteria inclusive of gram positive bacteria, some gram negative bacteria, anaerobic bacteria, Mycoplasma, Chlamidia and *Helicobacter pylori*, and because of its high stability in the acidic environment of the stomach, it can be orally administered to treat respiratory organ diseases, and also to prevent recurrence of ulcer when used in a combination with other medicines:

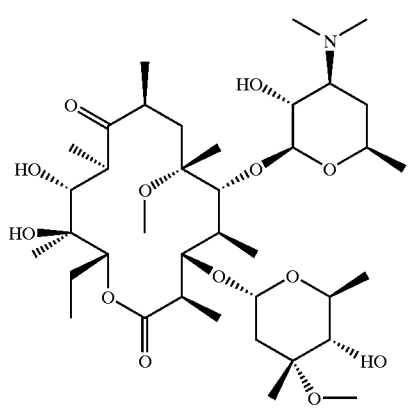

(I)

It has been discovered that clarithromycin exists in at least three distinct crystalline forms, "Form 0", "Form I" and "Form II", as described in International Publication Nos. WO 98-04573, WO 98-04574 and WO 98-31699. The crystal forms can be identified by infrared spectroscopy, differential scanning calorimetly and powder X-ray diffraction spectrophotometry. Form II, which is thermodynamically more stable than Form I, is used in the drug formulations currently on the market, and Form 0 is a solvate having an incorporated crystallizing solvent molecule.

Form II crystals clarithromycin have been typically prepared by any of three methods, as summarized in the schematic drawing of FIG. 3:

Method 1) is to heat Form 0 or Form I crystals under a vacuum at a temperature ranging from 70 to 110° C. for a prolonged period of time to prepare Form II crystals (see International Publication Nos. WO 98-04573 and WO 98-31699), but this method has the problem of low productivity and high cost.

Alternatively, in Method 2), Form II crystals may be obtained by recrystallizing Form I crystals from chloroform/isopropyl ether (1:2) (see Merck Index 12th ed., pp. 395). In addition, in Method 3), Form II crystals may be obtained by recrystallizing Form I crystals from an organic solvent such as alkanol (except ethanol and isopropanol); hydrocarbon; ketone; carboxyl ester (except isopropyl acetate); ether; substituted or non-substituted benzene; an aprotic polar solvent; amine; a water-miscible organic solvent or a mixture of a water-miscible alkanol and water; a mixture of methanol and hydrocarbon, alkanol, ketone, carboxyl ester, ether or substituted or non-substituted benzene; a mixture of hydrocarbon and ketone, carboxyl ester, ether or substituted or non-substituted benzene, or a mixture of said organic solvent and water (see International Publication Nos. WO 98-04574).

However, Methods 2) and 3) have a problem in that because the conversion step of Form I to Form II does not enhance the clarithromycin purity, Form I crystals having an pharmaceutically allowable purity must be prepared in advance from crude clarithromycin, at the expense of reduced clarithromycin yield and high manufacturing cost. Further, Method 3) employs a hot-filter during the recrystallization step, but hot-filtration is not suitable for mass-production.

SUMMARY OF THE INVENTION

Accordingly, it is a primary object of the present invention to provide a high yield process for preparing Form II crystals of clarithromycin of a high purity.

In accordance with one aspect of the present invention, there is provided a method of preparing Form II crystals of clarithromycin of formula (I) comprising the steps of: (a) treating clarithromycin with formic acid in an organic solvent to give crystalline clarithromycin formate of formula (II) and (b) neutralizing the clarithromycin formate with a base in a mixture of water and a water-miscible organic solvent:

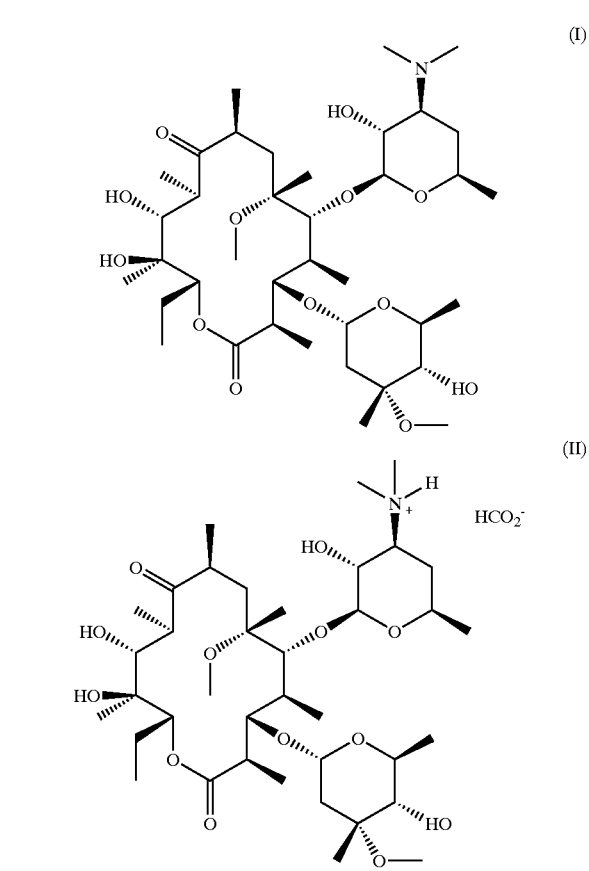

BRIEF DESCRIPTION OF THE DRAWINGS

The above and other objects and features of the present invention will become apparent from the following descrip

DETAILED DESCRIPTION OF THE INVENTION

Figure 1:
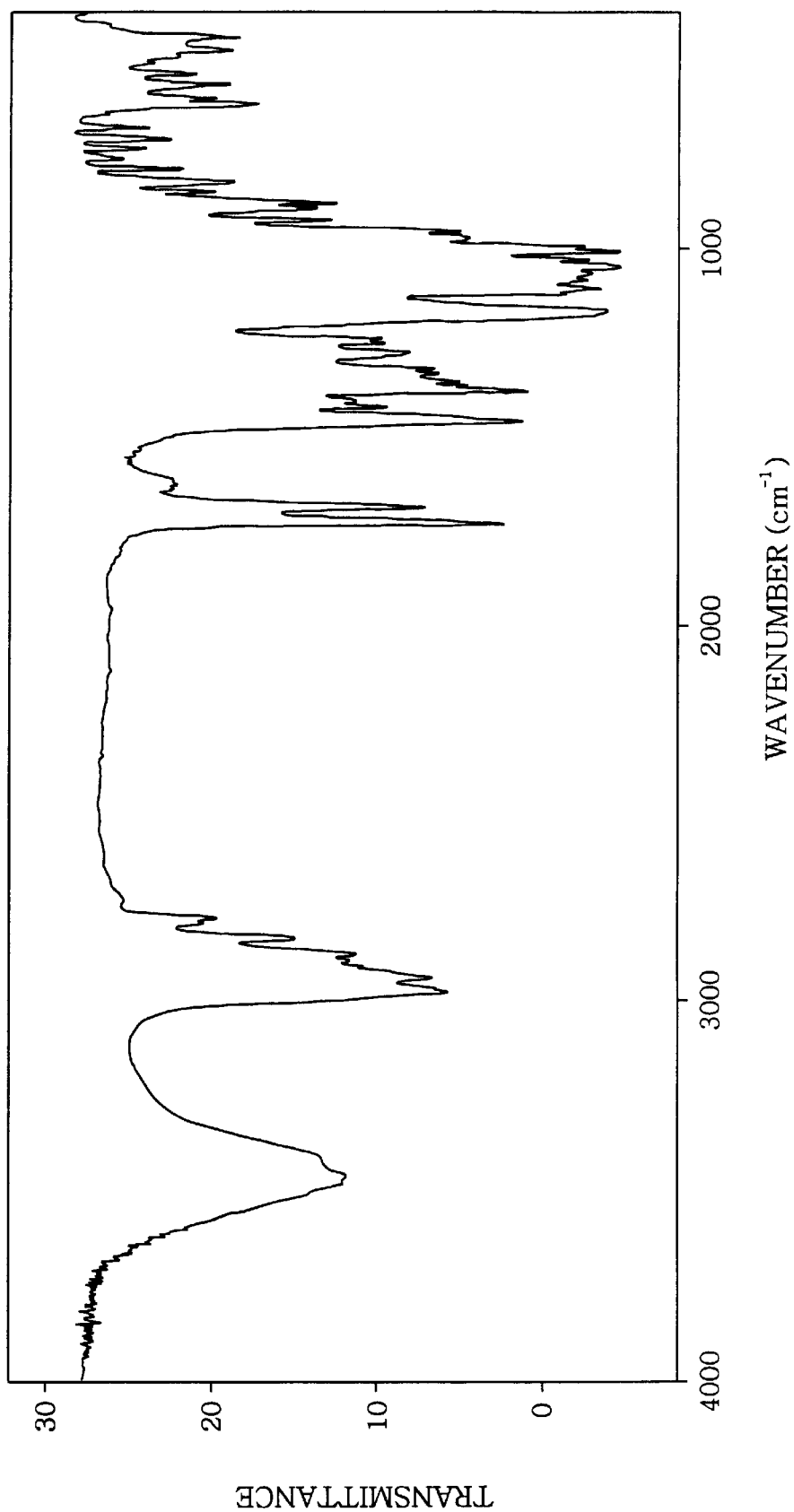
- FIGS. 1 and 2 represent the Infrared spectrum and powder X-ray diffraction spectrum of clarithromycin crystal Form II, respectively.

The term "clarithromycin" as used herein refers to refined crystal Form 0, Form I, any mixture of the three forms of crystals or a crude product obtained from a manufacturing process thereof. Representative methods of preparing clarithromycin are described in European Patent Nos. 158 467, 195 960, 260 938 and 272 110, and International Publication Nos. 97-36912 and 97-36913.

The steps (a) and (b) which constitute the method of the present invention are described in detail as follows;

Step (a): Preparation of Crystalline Clarithromycin Formate

In accordance with step (a) of the present invention, crystalline clarithromycin formate is prepared by treating clarithromycin dissolved in an organic solvent with formic acid and isolating crystals formed thereupon by filtration.

Specifically, clarithromycin is dissolved in an organic solvent at a temperature ranging from room temperature to the boiling point of the solvent for a period sufficient to make a solution or suspension. Then, formic acid, neat or dissolved in an organic solvent, is added to the solution or suspension in an amount ranging from 1 to 5 moles based on 1 mole of clarithromycin. The mixture may then be optionally kept at a temperature in the range of room temperature to the boiling point of the solvent for 10 minutes to 1 hour. The resulting mixture is cooled to a temperature in the range of −20° C. to room temperature for a period sufficient to precipitate formate crystals of clarithromycin. Finally, the precipitated crystals are filtered and dried in a conventional manner to give crystalline clarithromycin formate.

The organic solvents which may be employed in step (a) of the present invention are selected from the group consisting of (i) $C_{1-6}$ alkanol, (ii) $C_{3-6}$ ketone, (iii) $C_{3-8}$ carboxylic ester, (iv) $C_{1-6}$ nitrile, (v) $C_{4-10}$ ether, (vi) benzene, (vii) benzene substituted with at least one selected from the group consisting of $C_{1-3}$ alkyl, $C_{1-3}$ alkoxy, nitro and halogen, (viii) $C_{5-12}$ hydrocarbon, (ix) $C_{1-4}$ nitroalkane, (x) aprotic polar solvent, and (xi) a mixture thereof, and representative examples thereof include methanol, ethanol, propanol, isopropanol, butanol, isobutanol, tert-butanol, pentanol, hexanol, ethylene glycol, 1,2- or 1,3-propylene glycol, acetone, methyl ethyl ketone, 2-pentanone, 3-pentanone, methyl isobutyl ketone, methyl acetate, ethyl acetate, propyl acetate, isobutyl acetate, methyl propionate, acetonitrile, propionitrile, ethyl ether, isopropyl ether, methyl tert-butyl ether, tetrahydrofuran, dioxane, ethylene glycol dimethyl ether, ethylene glycol diethyl ether, diethylene glycol dimethyl ether, benzene, toluene, xylene, chlorobenzene, nitrobenzene, anisole, pentane, hexane, heptane, cyclohexane, nitromethane, nitroethane, nitropropane, N,N-dimethyl formamide, N,N-dimethyl acetamide, dimethyl sulfoxide, sulfolane and a mixture thereof, wherein preferred are acetone, methyl ethyl ketone, ethyl acetate, isopropyl acetate, acetonitrile, ethanol, isopropanol, tetrahydrofuran, 1,2-dimethoxyethane and a mixture thereof. Said organic solvent may contain water so long as it does not cause a phase separation. Also, a suitable mixture of a polar solvent and a nonpolar solvent may be advantageously employed.

If necessary, the clarithromycin formate crystals obtained in step (a) of the present invention may be further purified by recrystallization from said organic solvent.

Step (b): Preparation of Clarithromycin Crystal Form II

In accordance with step (b) of the present invention, Form II crystals of clarithromycin are prepared by treating the clarithromycin formate obtained in step (a) with a base in a mixture of water and a water-miscible organic solvent and isolating treated crystals by filtration.

Specifically, clarithromycin formate is dissolved in a mixture of water and a water-miscible organic solvent at a temperature in the range of room temperature to the boiling point of the solvent for a period sufficient to make a solution. Then, the solution is filtered and a base is added to the filtrate to neutralize and make pH of the solution 7 to 12. The solution may then be optionally kept at a temperature ranging from room temperature to the boiling point of the solvent for 10 minutes to 1 hour. The resulting solution is cooled to a temperature in the range of −20° C. to room temperature with or without stirring for a period sufficient to precipitate Form II crystals of clarithromycin. Finally, the precipitated crystals are filtered and dried in a conventional manner to give Form II crystals of clarithromycin.

The water-miscible organic solvent used in step (b) of the present invention may be selected from the group consisting of (i) $C_{1-6}$ alkanol, (ii) $C_{3-6}$ ketone, (iii) $C_{1-6}$ nitrile, (iv) diether and cyclic ether, (v) aprotic polar solvent, and (vi) a mixture thereof. Representative examples thereof include methanol, ethanol, propanol, isopropanol, butanol, isobutanol, tert-butanol, pentanol, hexanol, ethylene glycol, 1,2- or 1,3-propylene glycol, acetone, methyl ethyl ketone, 2-pentanone, 3-pentanone, methyl isobutyl ketone, acetonitrile, tetrahydrofuran, dioxane, ethylene glycol dimethyl ether, ethylene glycol diethyl ether, diethylene glycol dimethyl ether, N,N-dimethyl formamide, N,N-dimethyl acetamide, dimethyl sulfoxide, sulfolane and a mixture thereof, wherein preferred are acetone, acetonitrile, methanol, ethanol, isopropanol, tetrahydrofuran, dioxane, ethylene glycol dimethyl ether, N,N-dimethyl formamide and a mixture thereof.

Water and a water-miscible organic solvent may be mixed in a volume ratio ranging from 30:70 to 70:30.

The base used in the present invention is an inorganic base, or an organic base represented by $NR^1R^2R^3$ (wherein, $R^1$, $R^2$ and $R^3$ are each independently hydrogen or $C_{1-4}$ alkyl), and representative examples thereof include sodium hydroxide, potassium hydroxide, sodium carbonate, potassium carbonate, sodium bicarbonate, potassium bicarbonate, ammonia, methylamine, ethylamine, propylamine, butylamine, dimethylamine, diethylamine, trimethylamine, triethylamine and a mixture thereof, among which ammonia is preferred. The base, neat or dissolved in water, a water-miscible organic solvent or a mixture thereof, may be used in an amount needed to adjust pH of the solution in the range of 7 to 12.

The method of the present invention is very simple and provides pure Form II crystals of clarithromycin in a high yield, starting from e.g., crude clarithromycin.

The following Examples are given for the purpose of illustration only, and are not intended to limit the scope of the invention.

EXAMPLE 1

Preparation of Clarithromycin Formate from Clarithromycin of Varying Purity 7.48 g of clarithromycin (purity: 95.4%) was suspended in 70 ml of acetone, and 0.49 ml of formic acid was added thereto and refluxed for 30 minutes. The suspension was cooled to 0° C. and stirred for 2 hours. Then, the resulting crystals were filtered, washed with cold acetone and dried to give 7.42 g of clarithromycin formate (purity: 97.9%, yield: 94%).

Melting point: 197 to 199° C.

IR(KBr, cm$^{-1}$): 3470, 2975, 1731, 1692, 1459, 1377, 1170, 1052, 1011.

$^1$H-NMR (CDCl$_3$, ppm): 8.46(s, 1H, HCOO$^-$), 5.05(dd, 1H, 13-H), 4.92(d, 1H, 1"-H), 4.52(d, 1H, 1'-H), 4.01(dq, 1H, 5"-H), 3.76(d, 11H, 1-H), 3.74(dd, 1H, 3-H), 3.68(d, 1H, 5-H), 3.62(ddq, 1H, 5'-H), 3.36(dd, 1H, 2'-H), 3.34(s, 3H, 3"-OCH$_3$), 3.11~2.95(m, 3H, 10-H, 4"-H, 3'-H), 3.04(s, 3H, 6-OCH$_3$), 2.89(dq, 1H, 2-H), 2.63(s, 6H, 3'-N(CH$_3$)$_2$), 1.40 (s, 3H, 18-H), 0.85(t, 3H, 15-CH$_3$).

$^{13}$C-NMR (CDCl$_3$, ppm): 9.647(17-C), 10.981(15-C), 12.675(20-C), 16.330(16-C), 16.389(21-C), 18.390(19-C), 19.051(6"-C), 20.151(18-C), 21.398(14-C), 21.628(7"-C), 21.827(6'-C), 30.846(4'-C), 35.339(2"-C), 37.650(10-C), 39.478(4-C), 39.658(7-C), 40.036(7'-C, 8'-C), 45.396(2-C), 45.559(8-C), 49.851(8"-C), 50.995(22-C), 65.545(3'-C), 66.299(5'-C), 68.095(5'-C), 69.482(11-C), 71.164(2"-C), 73.217(3"-C), 74.662(12-C), 77.028(13-C), 78.222(4-C), 78.690(3-C), 78.999(6-C), 81.853(5-C), 96.601(1"-C), 102.797(1'-C), 169.083(HCOO$^-$), 176.237(1-C), 221.345(9-C).

The above procedure was repeated using less pure clarithromycin batches and the results are summarized in Table 1.

EXAMPLE 2

Preparation of Clarithromycin Formate from Clarithromycin of Varying Purity

The procedure of Example 1 was repeated except that ethyl acetate was used instead of acetone and that the mixture was stirred at room temperature for 1 hour before the cooling step. The results are shown in Table 1.

TABLE 1

| Organic solvent | | Purity (%) | | | |
|---|---|---|---|---|---|
| Ingredient | Volume (ml) | Clarithro-mycin Used | Clarithromycin formate obtained | Amount (g) | Yield (%) |
| Ex. 1 Acetone | 70 | 95.4 | 97.9 | 7.42 | 94 |
| | | 88.4 | 95.6 | 6.83 | 86 |
| | | 81.3 | 91.5 | 6.35 | 80 |
| Ex. 2 Ethyl acetate | 100 | 95.4 | 97.1 | 7.64 | 96 |
| | | 88.4 | 94.1 | 6.91 | 87 |
| | | 81.3 | 89.9 | 6.51 | 82 |

EXAMPLES 3 to 8

Preparation of Clarithromycin Formate from Crude Clarithromycin

In accordance with the method disclosed in International Publication No. 97-36913, 112.8 g of 2', 4"-O-bis(trimethylsilyl)erythromycin A 9-(tert-butyldimethyl)silyloxime (0.112 mole) was 6-O-methylated and then, removed the protecting and oxime groups, and worked-up by extraction to obtain 89.7 g of a crude clarithromycin product (a foam containing 42.5 g of clarithromycin).

89.7 g of the crude clarithromycin product (0.057 mole as clarithromycin) was suspended in 200 ml of acetone, 6.33 ml of formic acid (0.17 mole) was added thereto and refluxed for 30 minutes. The suspension was cooled to 0° C. and stirred for 2 hours. Then, the resulting crystals were filtered, washed with cold acetone and dried to give 48.9 g of clarithromycin formate (purity: 80.8%, yield: 55%) (Example 3).

In each of Examples 4 to 8, the procedure of Example 3 was repeated except that a different organic solvent was used instead of acetone. The results according to Examples 3 to 8 are shown in Table 2.

TABLE 2

| Organic solvent | | Amount | Yield | Purity |
|---|---|---|---|---|
| Ingredient | Volume (ml) | (g) | (%) | (%) |
| Ex. 3 | Acetone | 200 | 48.9 | 55 | 80.8 |
| Ex. 4 | Ethyl acetate | 200 | 50.0 | 56 | 79.1 |
| Ex. 5 | Acetonitrile | 200 | 46.6 | 52 | 82.1 |
| Ex. 6 | 2-Butanone | 200 | 41.8 | 47 | 80.1 |
| Ex. 7 | Tetrahydrofuran | 150 | 40.0 | 45 | 84.3 |
| Ex. 8 | 1,2-Dimethoxyethane | 200 | 51.1 | 58 | 78.2 |

EXAMPLES 9 and 10

Recrystallization of Clarithromycin Formate 54.0 g of clarithromycin formate (purity: 82.1%) obtained in Example 5 was suspended in 400 ml of acetone and refluxed for 1 hour. The suspension was cooled to 5° C. and stirred for 2 hours. Then, the resulting crystals were filtered and dried to give 44.3 g of refined clarithromycin formate (purity: 93.8%, recovery: 82%) (Example 9).

In Example 10, the procedure of Example 9 was repeated using ethyl acetate instead of acetone, to give refined clarithromycin formate. The results according to Examples 9 and 10 are shown in Table 3.

TABLE 3

| | Organic solvent | Amount (g) | Recovery (%) | Purity (%) |
|---|---|---|---|---|
| Ex. 9 | Acetone | 44.3 | 82 | 93.8 |
| Ex. 10 | Ethylacetate | 45.4 | 84 | 91.6 |

EXAMPLES 11 to 20

Preparation of Form II Crystals of Clarithromycin from Clarithromycin Formate 7.94 g of clarithromycin formate (purity: 93.8%) obtained in Example 9 was suspended in a mixture of 50 ml of water and 50 ml of ethanol, and filtered to remove impurities. The filtrate was heated to 55° C. and 1.2 ml of concentrated ammonia was added thereto to adjust the solution pH to 10. The solution was slowly cooled to room temperature and stirred for 3 hours. Then, the resulting crystals were filtered and dried overnight in a vacuum oven at 55° C. to give 6.91 g of clarithromycin crystal Form II (purity: 97.5%, yield: 92%) (Example 11).

In each of Examples 12 to 20, the procedure of Example 11 was repeated except that a different mixed solvent was used instead of water-ethanol (50:50). The results according to Examples 11 to 20 are shown in Table 4.

Figure 2:
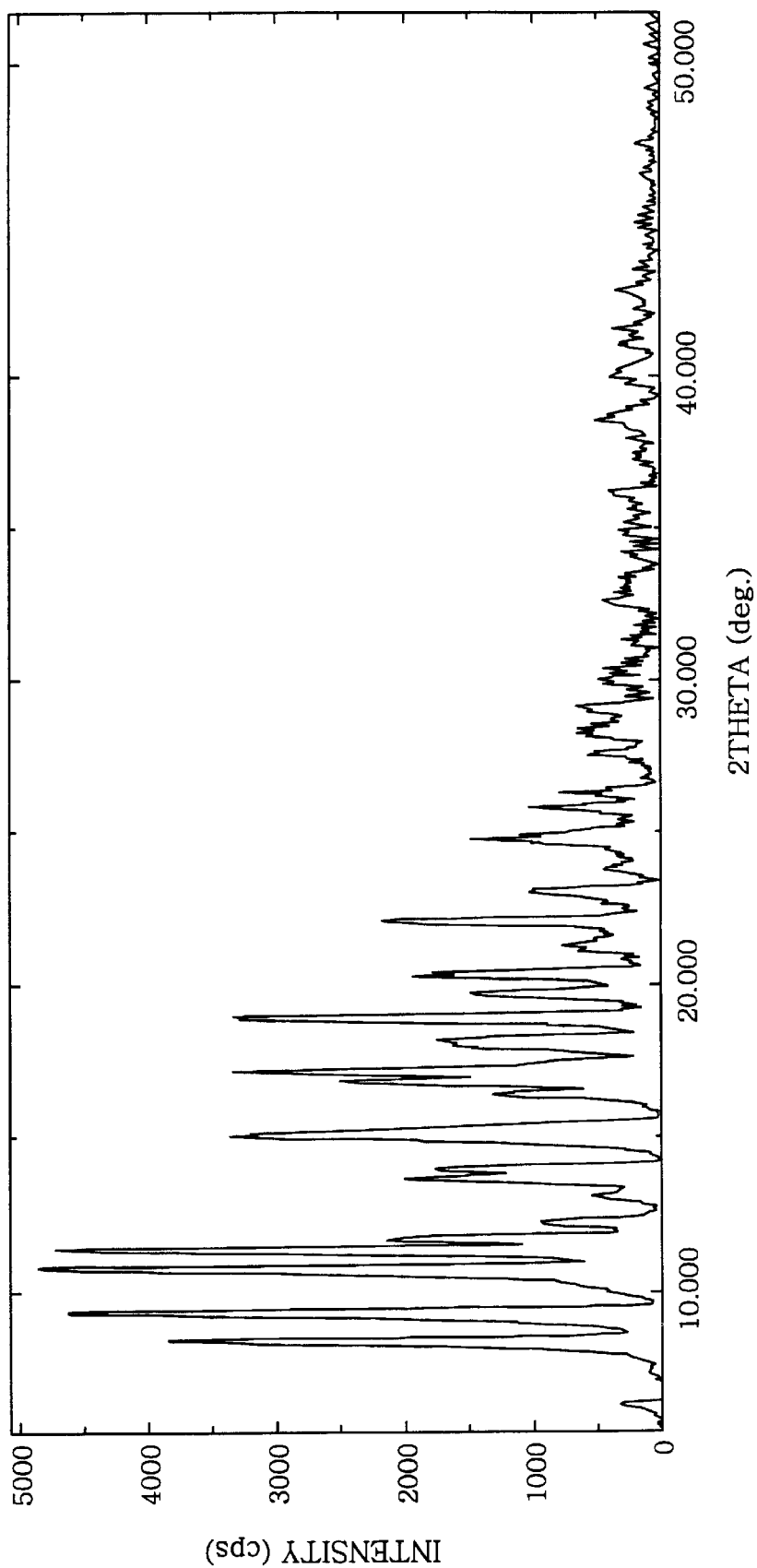
Figure 3:
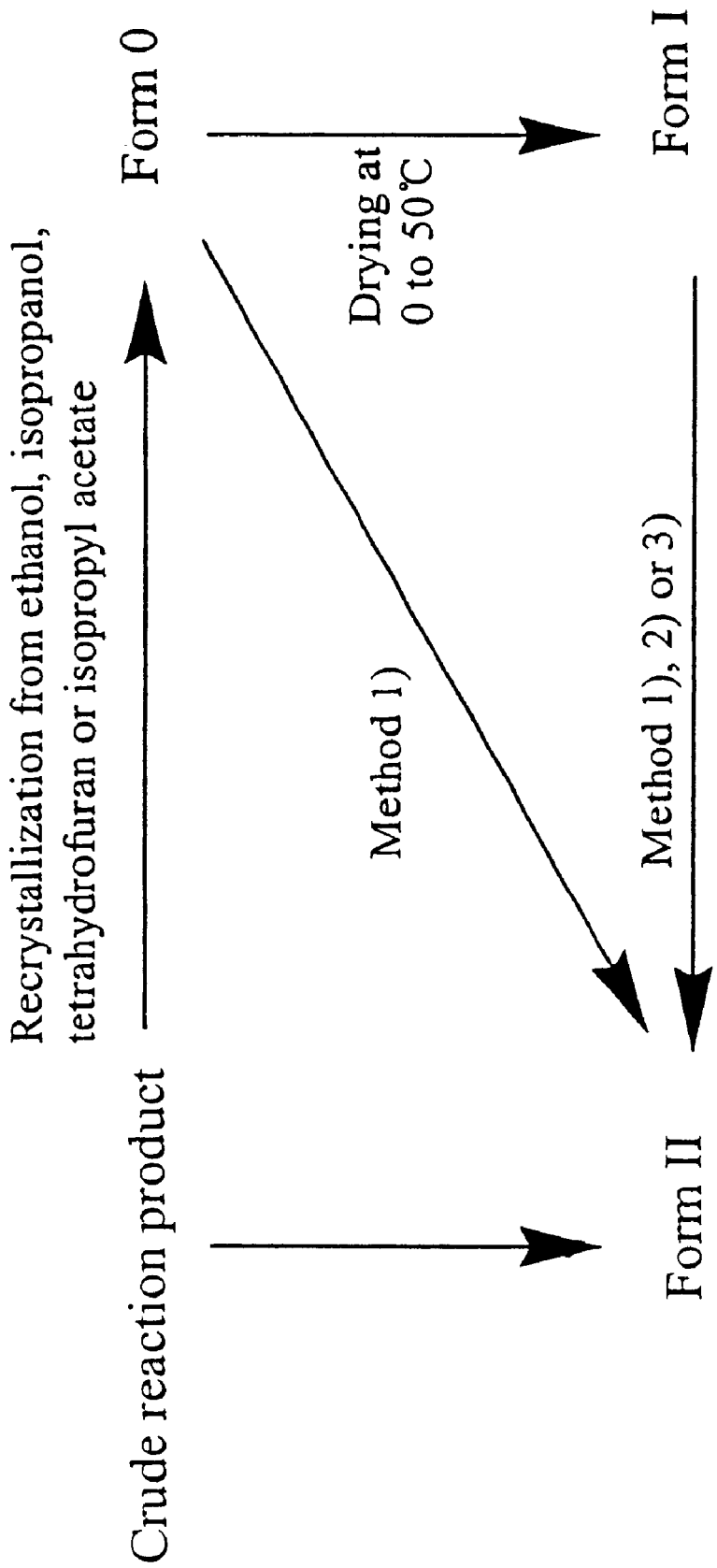
FIG. 3 schematic drawing summarizes three methods by which Form II crystals clarithromycin have been typically prepared.

The Infrared spectrum and powder X-ray diffraction spectrum of each clarithromycin obtained in Examples 11 to 20 were identical to those of clarithromycin crystal Form II shown in FIG. 1 and 2.

TABLE 4

| | Organic solvent:Water (ml:ml) | Amount (g) | Yield (%) | Purity (%) |
|---|---|---|---|---|
| Ex. 11 | Ethanol:Water (50:50) | 6.91 | 92 | 97.5 |
| Ex. 12 | Ethanol:Water (60:30) | 6.38 | 85 | 96.8 |
| Ex. 13 | Ethanol:Water (50:100) | 6.80 | 91 | 96.5 |
| Ex. 14 | Isopropanol:Water (50:50) | 6.70 | 89 | 97.7 |
| Ex. 15 | Methanol:Water (100:50) | 6.30 | 84 | 97.1 |
| Ex. 16 | Acetone:Water (50:50) | 6.70 | 90 | 98.1 |
| Ex. 17 | Acetonitrile:Water (50:50) | 6.30 | 84 | 97.3 |
| Ex. 18 | Tetrahydrofuran:Water (50:150) | 6.50 | 87 | 97.6 |
| Ex. 19 | 1,2-Dimethoxyethane:Water (50:50) | 6.80 | 91 | 95.9 |
| Ex. 20 | N,N-Diemethylformamide:Water (75:50) | 6.30 | 84 | 96.5 |

Comparative Example 89.7 g of a crude clarithromycin product (containing 42.5 g of clarithromycin) which was obtained in accordance with the method disclosed in International Publication No. 97-36913 was crystallized from ethanol and dried to give 39.0 g of clarithromycin crystal Form I (purity: 78.1%, yield: 47%).

38.0 g of clarithromycin crystal Form I (purity: 78.1%) was suspended in 300 ml of ethanol and refluxed for 1 hour to dissolve most of the crystals. The solution was hot-filtered to remove insoluble ingredients, and the filtrate was cooled to 10° C. and stirred for 2 hours. Then, the resulting crystals were filtered and dried in a vacuum oven at 50° C. to give 29.3 g of refined clarithromycin crystal Form I (purity: 91.7%, recovery: 77%).

Then, 20 g of refined clarithromycin crystal Form I (purity: 91.7%) was suspended in 100 ml of ethyl acetate and refluxed for 1 hour. Insoluble ingredients were removed by hot-filtration, and 15 ml of ethyl acetate was added to the filtrate and refluxed. The solution was cooled to 50° C., and 100 ml of isopropyl ether was added thereto and cooled to 5° C. The resulting crystals were filtered and dried to give 14.3 g of clarithromycin crystal Form II (purity: 95.2%, yield: 77%).

As shown above, the method of the present invention is capable of providing higher purity Form II crystals of clarithromycin in a higher yield, as compared with the conventional method.

While the embodiments of the subject invention have been described and illustrated, it is obvious that various changes and modifications can be made therein without departing from the spirit of the present invention which should be limited only by the scope of the appended claims.

What is claimed is:

1. A method of preparing Form II crystals of clarithromycin of formula (I) comprising the steps of: (a) treating clarithromycin with formic acid in an organic solvent to give crystalline clarithromycin formate of formula (II) and (b) neutralizing the clarithromycin formate with a base in a mixture of water and a water-miscible organic solvent:

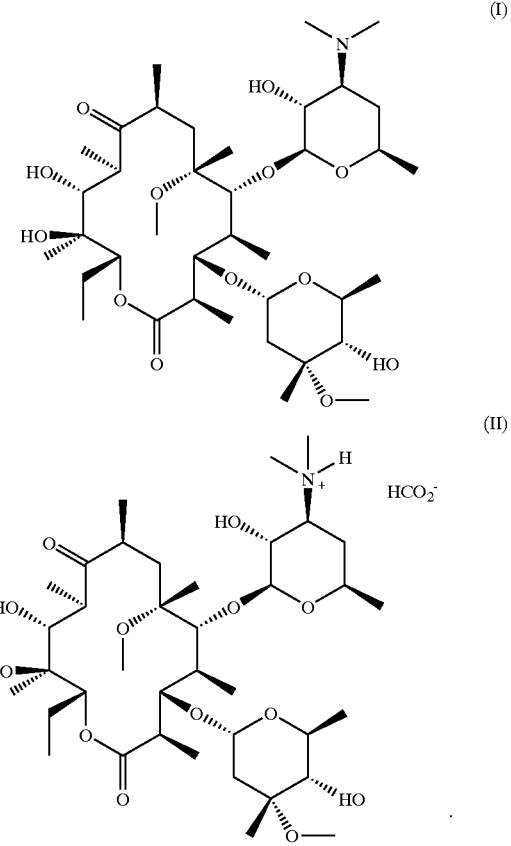

2. The method of claim 1, wherein the organic solvent used in step (a) is selected from the group consisting of (i) $C_{1-6}$ alkanol, (ii) $C_{3-6}$ ketone, (iii) $C_{3-8}$ carboxylic ester, (iv) $C_{1-6}$ nitrile, (v) $C_{4-10}$ ether, (vi) benzene, (vii) benzene substituted with at least one of the substituents selected from $C_{1-3}$ alkyl, $C_{1-3}$ alkoxy, nitro and halogen, (viii) $C_{5-12}$ hydrocarbon, (ix) $C_{1-4}$ nitroalkane, (x) aprotic polar solvent, and (xi) a mixture thereof.

3. The method of claim 1, wherein formic acid is used in an amount ranging from 1 to 5 moles based on 1 mole of clarithromycin.

4. The method of claim 1, wherein the water-miscible organic solvent used in step (b) is selected from the group consisting of (i) $C_{1-6}$ alkanol, (ii) $C_{3-6}$ ketone, (iii) $C_{1-6}$ nitrile, (iv) diether and cyclic ether, (v) aprotic polar solvent, and (vi) a mixture thereof.

5. The method of claim 4, wherein the water-miscible organic solvent is acetone, acetonitrile, methanol, ethanol, isopropanol, tetrahydrofuran, dioxane, ethylene glycol dimethyl ether, N,N-dimethyl formamide or a mixture thereof.

6. The method of claim 1, wherein the mixture is composed of water and a water-miscible organic solvent in a volume ratio of 30:70 to 70:30.

7. The method of claim 1, wherein the base is selected from the group consisting of alkali metal hydroxide, alkali metal carbonate, alkali metal bicarbonate, $NR^1R^2R^3$ (wherein, $R^1$, $R^2$ and $R^3$ are each independently hydrogen or $C_{1-4}$ alkyl), and a mixture thereof.

8. The method of claim 7, wherein the base is ammonia.

9. The method of claim 1, wherein the neutralization step is conducted to a pH in the range of 7 to 12.

* * * * *